United States Patent
Krause et al.

(10) Patent No.: US 12,403,228 B2
(45) Date of Patent: Sep. 2, 2025

(54) MONITORING DEVICE FOR RECIRCULATION ANALYSIS

(71) Applicant: B. Braun Avitum AG, Melsungen (DE)

(72) Inventors: Silvie Krause, Melsungen (DE); Henrik Wolff, Melsungen-Adelshausen (DE); Marten Jakob, Klein Lengden (DE)

(73) Assignee: B. Braun Avitum AG, Melsungen (DE)

( * ) Notice: Subject to any disclaimer, the term of this patent is extended or adjusted under 35 U.S.C. 154(b) by 925 days.

(21) Appl. No.: 17/433,365

(22) PCT Filed: Feb. 25, 2020

(86) PCT No.: PCT/EP2020/054833
§ 371 (c)(1),
(2) Date: Aug. 24, 2021

(87) PCT Pub. No.: WO2020/173900
PCT Pub. Date: Sep. 3, 2020

(65) Prior Publication Data
US 2022/0168482 A1    Jun. 2, 2022

(30) Foreign Application Priority Data
Feb. 25, 2019  (DE) ............... 10 2019 104 738.2

(51) Int. Cl.
*A61M 1/16*    (2006.01)
*G16H 20/40*    (2018.01)

(52) U.S. Cl.
CPC .......... *A61M 1/1619* (2014.02); *G16H 20/40* (2018.01)

(58) Field of Classification Search
CPC ................ A61M 1/1619; G16H 20/40
(Continued)

(56) References Cited

U.S. PATENT DOCUMENTS

| 6,117,099 A | 9/2000 | Steuer et al. |
| 7,674,236 B2 | 3/2010 | Daniel et al. |

(Continued)

FOREIGN PATENT DOCUMENTS

| CN | 101098721 A | 1/2008 |
| CN | 103721306 A | 4/2014 |

(Continued)

OTHER PUBLICATIONS

Vogt, G. ; Control and safety systems for the microspheres based detoxification system; Proceedings of the 20th Annual International Conference of the IEEE Engineering in Medicine and Biology Society. vol. 20 Biomedical Engineering Towards the Year 2000 . . . (Year: 1998).*

(Continued)

*Primary Examiner* — Hiep V Nguyen
(74) *Attorney, Agent, or Firm* — Christopher A. Rothe; CM Law (57) ABSTRACT

A monitoring method for an extracorporeal blood treatment machine, a monitoring device of an extracorporeal blood treatment machine, and an extracorporeal blood treatment machine including a monitoring device. The monitoring device is configured to detect a signal representing a concentration of pollutants in a used dialysis liquid, to automatically evaluate a signal course with respect to at least one predetermined indicator for an existing recirculation, and to automatically initiate a recirculation measurement or automatically output a request for initiating a recirculation measurement to a user upon determination of the at least one indicator.

11 Claims, 3 Drawing Sheets

(58) Field of Classification Search
USPC .............................................................. 705/2
See application file for complete search history.

(56) References Cited

U.S. PATENT DOCUMENTS

| | | | |
|---|---|---|---|
| 9,233,199 B2 | 1/2016 | Krause et al. | |
| 2001/0050256 A1* | 12/2001 | Krivitski | A61M 1/3663 600/504 |
| 2007/0249983 A1* | 10/2007 | Tonelli | A61M 1/1643 604/6.09 |
| 2013/0274642 A1* | 10/2013 | Soykan | A61B 5/389 604/5.01 |
| 2014/0102983 A1 | 4/2014 | Meibaum et al. | |
| 2019/0083694 A1 | 3/2019 | Kopperschmidt et al. | |

FOREIGN PATENT DOCUMENTS

| | | | | |
|---|---|---|---|---|
| DE | 102015016854 A1 | | 6/2017 | |
| EP | 2783716 A1 | | 10/2014 | |
| EP | 2783715 B1 | | 5/2017 | |
| JP | 2019080932 A | * | 5/2019 | ............ A61M 1/154 |
| WO | WO-9962574 A1 | * | 12/1999 | .............. A61M 1/16 |

OTHER PUBLICATIONS

Written Opinion received in International Application No. PCT/EP2020/054833 dated May 28, 2020, with translation, 12 pages.

Search Report received in German Application No. 10 2019 104 738.2 dated Nov. 15, 2019, with translation, 13 pages.

Search Report received in International Application No. PCT/EP2020/054833 dated May 28, 2020, with translation, 8 pages.

B. Braun Avitum AG: Adimea—Precise real-time measurement of a dialysis dose, Mar. 2014, with translation, 24 pages.

Office Action received in Chinese Application No. 202080023898.8 dated Feb. 28, 2025, with translation, 12 pages.

* cited by examiner

MONITORING DEVICE FOR RECIRCULATION ANALYSIS

CROSS-REFERENCE TO RELATED APPLICATIONS

This application is the United States national phase entry of International Application No. PCT/EP2020/054833, filed Feb. 25, 2020, and claims the benefit of priority of German Application No. 10 2019 104 738.2, filed Feb. 25, 2019. The contents of International Application No. PCT/EP2020/054833 and German Application No. 10 2019 104 738.2 are incorporated by reference herein in their entireties.

FIELD

The present disclosure relates to a monitoring device of an extracorporeal blood treatment machine, which in the course of a dialysis treatment is configured to detect a signal that represents a concentration of pollutants in a used dialysis liquid, as well as to an associated monitoring method and an extracorporeal blood treatment machine including such monitoring device.

BACKGROUND

In extracorporeal blood treatments, in particular dialysis treatments, blood is taken from a blood vessel of a patient at a blood collection site via a shunt, cleaned in an extracorporeal blood treatment machine, in particular a dialysis machine, and then reintroduced into the patient via the shunt downstream of the blood collection site. It can happen that already purified blood in the shunt flows back to the collection site and is reintroduced into the extracorporeal blood treatment machine. Stated in other words, a recirculation occurs through which the blood to be purified, which is being introduced into the extracorporeal blood treatment machine, is "diluted" by recirculated, already purified blood, with the result that the blood treatment deteriorates. Accordingly, recirculation is an important issue in extracorporeal blood treatments. The occurrence of a recirculation should be detected as quickly and reliably as possible and countermeasures taken immediately.

In order to determine a recirculation without any doubt, there are various measurement techniques that can be carried out selectively for individual measurements, for example a system called Transonic that is available on the market, but which do not allow a recirculation to be reliably detected immediately as soon as it occurs. There are also online measurement methods, which, however, entail high costs and equipment expenditures.

In extracorporeal blood treatment, in addition to recirculation, a large number of other parameters are monitored and adjusted. An example for this is the monitoring of the treatment effectiveness/treatment progress of an extracorporeal blood treatment machine, in particular dialysis machine, on the basis of a Kt/V value (with K=clearance, t=dialysis time and V=urea distribution volume), which is calculated from spectroscopic measurements and which represents the reduction of the substance concentration of urinary excreted substances in the used dialysis liquid. An example for this is the ADIMEA™ brand system from B. Braun, which provides online information about the treatment progress and enables a highly accurate real-time measurement of the Kt/V value during treatment, in particular a Kt/V value or an spKt/V value (single spool Kt/V value). For this purpose, the ADIMEA™ brand system from B. Braun determines a UV absorption in the dialysate outflow (i.e. in the used dialysis liquid) as a measure of the urea concentration in the patient's plasma, which is proportional to the concentration of UV-absorptive (urinary excreted) substances in the patient's blood. This proportionality also occurs at a constant degree of recirculation, but wherein a corresponding proportionality factor may change.

Accordingly, it is known that certain behavioral patterns of the Kt/V value, in particular of the Kt/V value (e.g. a sudden increase in a corresponding curve after a reduction of the blood flow rate), may indicate an existing recirculation. However, the Kt/V value depends on a number of other factors, such as patient-specific parameters, various problems in the machine's piping system, various operating parameters of the extracorporeal blood treatment machine and the set dialysis dose that can be adjusted during treatment. Furthermore, the behavior patterns indicating a recirculation either occur only with a specific parameter change, such as in the above-mentioned reduction of the blood flow rate, and thus do not permit online measurement, or are difficult or impossible to detect due to the large number of parameters involved. As described above, the state of the art provides either for the use of additional complex measuring instruments for online measurement or, for example, for individual measurements to be carried out at regular intervals which, although reliable and accurate, have the consequence that recirculation may not be immediately detectable. As a result, the development of recirculation monitoring devices has so far focused heavily on improving measuring devices for online measurement.

SUMMARY

The task underlying the invention is to reduce the disadvantages of the state of the art. In particular, a simple, cost-effective monitoring device for an extracorporeal blood treatment machine is to be provided, which makes it possible to automatically, quickly and reliably detect suspicious facts regarding a possibly existing recirculation, in order to prevent, for instance, a patient from receiving a too low dialysis dose in the long term. Subsequently, a single measurement can be used to verify or falsify whether there is actually a recirculation.

In analyzing problems of recirculation measurements of the state of the art described above, it was recognized that these can also be solved without a determination of a recirculation immediately after its occurrence (which is not achievable by single measurements) or a reliable determination and measurement of an existing recirculation (which is not possible by means of a Kt/V signal) being necessary, in order to nevertheless enable both a fast and a reliable determination of a recirculation.

The task underlying the invention is solved by a monitoring device of an extracorporeal blood treatment machine, which is configured to detect a signal which (essentially continuously) represents a concentration of pollutants in used dialysis liquid. This monitoring device is also configured to automatically evaluate a course of the signal or signal course with respect to at least one predetermined indicator/signal course indicator/signal course pattern for an existing recirculation and to output a trigger signal when determining the at least one indicator, which automatically initiates a recirculation measurement or automatically outputs a request to initiate a recirculation measurement to a user. A prerequisite for the selection of the signal as well as of the measuring cell (e.g. the Kt/V measuring cell of the ADIMEA™ brand system from B. Braun) capturing the signal is that the signal must be very stable and reliably measurable. A recirculation measuring cell, which is intended to perform the recirculation measurement preferably as a single measurement, can accurately and reliably determine or verify an existing recirculation. Thus, advantageously, any occurring recirculation can be detected immediately and it can be avoided that a patient receives a too low dialysis dose in the long run.

In other words, signal courses representing the concentration of pollutants in used dialysis liquid in an extracorporeal blood treatment were analyzed, particularly with regard to recirculation, and various indicators were derived from the signal course, which may be an indication that recirculation was present in the patient currently being treated. For example, the signal course may indicate a significantly reduced dialysis efficiency, i.e. a much slower than expected decrease in the concentration of pollutants if there is constant recirculation. This can be justified by the fact that the blood to be purified passing through the extracorporeal blood treatment machine is diluted by the already purified, recirculated blood and thus relatively few pollutants can be removed. On the other hand, the signal course may give the impression that the concentration of pollutants drops significantly faster than expected or that the dialysis efficiency is significantly higher than expected, which may indicate an increasing recirculation of already purified blood. Furthermore, an unsteady, volatile signal course may occur, for example due to turbulences in the shunt through which the extracorporeal treatment machine is connected to the patient, or to patient-related parameters such as frequent movement of the patient. Such turbulences or frequent patient movements can also promote recirculation. Accordingly, a "jumping", unsteady signal course can also indicate recirculation. Furthermore, a single, high increase of the signal course can occur during the onset of recirculation. It goes without saying that these signal courses indicative of a recirculation can also superimpose each other.

The indicators thus determined were deposited stored in the monitoring device according to the invention, in particular in a storage unit of the same, so that the monitoring device can automatically isolate and recognize the indicators during the signal measurement. However, since the indicators can also have a multitude of other causes, a trigger or a trigger signal is then output after determining the present indicator, which trigger or a trigger signal, for example, automatically initiates an exact individual measurement and preferably outputs a warning signal if the presence of a recirculation is confirmed. Alternatively, the trigger or trigger signal automatically issues a message to a user that such a single measurement should be initiated manually. In this way it is possible to use the immediacy of the signal measurement without having to forego a reliable determination of the recirculation. Subsequently, the end results of the recirculation or individual measurements initiated or triggered in this way are preferably stored in a history for automatic or manual evaluation or control. In addition, it is further preferred that automatically triggered/initiated measurements are displayed e.g. by different colors or markers than the manually triggered/initiated measurements.

Preferably, the signal represents a Kt/V value, in particular a Kt/V value determined with the ADIMEA™ brand system from B. Braun, or is a raw signal, preferably intensity and/or absorption values of a spectroscopic measurement, on the basis of which the Kt/V value can be calculated. With extracorporeal blood treatments, the Kt/V value is determined by default in various ways, e.g. via the ADIMEA™ brand system from B. Braun, which enables a very stable, reliable online measurement of the Kt/V signal.

It has proven to be useful to differentiate the signal in order to calculate a differential signal. This differential signal can then be compared with at least one threshold value wherein, as one of the indicators for an existing recirculation, a certain frequency (e.g. more than three or four times) or duration of threshold value overruns preferably within a certain time period is usable. In this way, in particular a jumping signal course and possibly a significantly stronger decrease of the concentration of pollutants than expected can be detected. Alternatively or additionally, a one-time threshold value overrun of the same or another, higher threshold value can be detected as one of the indicators for an existing recirculation. In particular, this indicates a sudden, high increase in the signal course. Alternatively or additionally, a certain frequency or duration of undershoots of a further, lower threshold value, preferably within a certain period of time, can be used as an indicator. This can be attributed to a jumping signal course as well as a significantly weaker decrease of the concentration of pollutants than expected. Accordingly, from a simple differentiation of the signal (from the differential signal) different indicators can be derived for an occurring recirculation, which is a simple operation requiring little computing power.

Preferably, the threshold value(s) depend(s) on a desired treatment time as well as a desired signal value and/or a theoretically calculated signal value. For example, a Kt/V Watson value can be used for the complete treatment or parts of the treatment. With the Kt/V Watson value, the urea distribution volume (V) is calculated according to a so-called Watson formula, wherein the clearance (K) is determined either based on the properties of the dialyzer and/or the blood and, if applicable, of the dialysis liquid flow or according to a table or similar. This means that the signal course is compared with an ideal or theoretical signal course and a certain degree of deviation from this ideal or theoretical signal course is used as an indicator for an existing recirculation.

Alternatively or additionally, the threshold value(s) depend(s) on the desired treatment time and a signal value of one or more previous extracorporeal blood treatment(s) of the specific patient, for example on an average of such signal values. In this way, patient-specific parameters can also be taken into account. As a reference for the calculation of the threshold value(s), for example the Kt/V values at certain points in time, a Kt/V signal course or its form, a number of slope changes of the signal course, a level of deviations between different signal courses, a typical variability for the specific patient, averages or the like can be taken into account. For example, a number of acceptable signal jumps of a Kt/V signal of the specific patient can be adjusted, for example, if he/she is known to be frequently restless without a recirculation having been determined so far.

Further preferred, the monitoring device may be arranged to calculate, from the signal, an expected treatment time at which a desired signal value is expected to be reached and to compare it with a desired treatment time, wherein a significant fall below and/or a significant rise above the desired treatment time serves as an indicator for an existing recirculation. In other words, an intersection of the signal with a desired signal value or a desired concentration of pollutants is calculated based on its mean slope. A clear undercutting (e.g. an expected treatment time of 60% of the desired treatment time) shows that the concentration of pollutants drops much faster than expected, and a clear exceeding shows that the concentration of pollutants drops much slower than expected. This is particularly advantageous, since this monitoring of the expected treatment time also makes it possible to evaluate signal courses with significant jumps simply in terms of their mean slope or the expected treatment duration.

Alternatively or additionally, it can be advantageous to compare the signal course with known, previously stored patterns of a signal course that occur during an existing recirculation, and to recognize a sufficient correspondence of the signal with the known patterns as an indicator for an existing recirculation. Such previously stored patterns can be signal courses or templates that are typical for a recirculation, e.g. with a sudden, high increase or frequent jumps. In this case, the monitoring device is arranged for comparing the signal course frequently or continuously with these patterns, for example by cross-correlation calculation, and to recognize sufficient correspondence as one of the indicators for an existing recirculation. This procedure is particularly advantageous if the raw signal, in particular an intensity and/or absorption signal, is used to determine the indicator, since some signal processing steps that may require a lot of computing can be dispensed with in this way.

According to one aspect of the present invention, the monitoring device can be configured to initiate a plausibility check after determining the at least one indicator, preferably immediately afterwards. This means that an additional check is initiated as soon as an available indicator has been determined, and in said additional check it is checked whether the indicator can actually indicate a possible recirculation or whether its presence is probable, or whether there are other parameters, if any, that could have triggered the occurrence of the indicator. This is advantageous, as unnecessary recirculation measurements can be avoided in this way, which means that the course of the extracorporeal blood treatment and/or its monitoring is less disturbed.

Preferably, it is possible within the framework of the plausibility check to compare the occurrence of the indicator with other sensor data, preferably a venous pressure. If, for example, there occurs a frequently jumping signal course (in particular a Kt/V course), possibly simultaneously with strong fluctuations of the arterial and venous pressure recorded by corresponding pressure sensors, pressure readings of a venous pressure sensor are analyzed. If these pressure readings exceed a defined, possibly patient-individual limit value, such as 150 mmHg, optionally immediately after such signal courses were observed or simultaneously with it, this is an additional indication of a change in the vascular access or a suboptimal needle position. Accordingly, in this case a plausibility check result is positive and a recirculation measurement is automatically initiated or a corresponding request is automatically issued to the user.

Alternatively or additionally, the occurrence of the indicator can be compared with a change in an operational state or parameter of the extracorporeal blood treatment machine. For example, a check is made whether an operating parameter was changed (especially immediately) before the indicator occurred and whether the change of the signal course associated with the indicator can be attributed to this changed operating parameter, which would lead to a negative plausibility check result. Further, for example, it may increase the suspicion of recirculation and thus produce a positive plausibility check result if the indicator of a concentration of pollutants that is clearly too large immediately follows a previous reduction in the blood flow rate.

It is further possible to configure the monitoring device in such a way that it determines several of the indicators and compares them within the framework of the plausibility check. Thus, the monitoring device checks in this case if several of the indicators described above occur simultaneously, such as a frequently jumping signal course in combination with a clearly too fast or too slow drop in the concentration of pollutants, and outputs a positive plausibility check result if this is the case, or alternatively outputs a negative plausibility check result if no other indicator has been determined. This type of plausibility check can be performed based solely on the signal course. This means that no matching with other sensors or the control of the extracorporeal blood treatment machine is necessary.

Preferably, the monitoring device is also adapted to initiate further measurements in a case where the recirculation measurement shows that there is no recirculation, in order to determine potentially other causes for the presence of the at least one indicator.

Furthermore, the task underlying the invention is solved by a monitoring method of a monitoring device which corresponds to the monitoring device according to the invention described above. The monitoring method comprises the following steps: detecting a signal representing a concentration of pollutants in a used dialysis liquid, automatically evaluating the course of the signal with respect to at least one predetermined indicator for an existing recirculation, and automatically initiating a recirculation measurement or outputting an automatic request for initiating a recirculation measurement to a user, if the at least one indicator has been determined, in particular via a trigger or a trigger signal. Preferably, a step may also be provided according to which a plausibility check is initiated after, preferably immediately after, the at least one indicator has been determined.

In addition, the task underlying the invention is solved by an extracorporeal blood treatment machine, preferably a dialysis machine, comprising a monitoring device described above.

With regard to the more detailed configuration of the monitoring method described above as well as of the extracorporeal blood treatment machine, reference is made to above description of the monitoring device according to the invention.

In other words, a recirculation directly affects the course of a Kt/V curve (Kt/V as f(t)). Since this course is preferably monitored by the ADIMEA™ brand system from B. Braun, a deviation from the expected course of the curve may be due to recirculation. Indications for a recirculation can be, for instance, jumps in the curve progression, a very flat, monotonous course, a gradient which is too large, or the like. Various measures can serve as plausibility check, such as a comparison with stored curve progressions, a comparison with values determined according to another method (e.g. Kt/V-Watson), in addition a matching with the current machine status, etc. The derivation of the Kt/V curve, in particular the spKt/V curve, can be used in conjunction with a defined threshold value to determine an 'unsteady' increase. A repeated exceeding of the threshold value then serves as trigger for a recirculation measurement.

Or to put it another way, it is possible to continuously monitor the Kt/V curve, especially the spKt/V curve, or its derivatives during treatment and use this derivative to test an unsteady rise of the curve based on a threshold value. Peaks or peak values that exceed the threshold value can be counted. If the threshold value is exceeded several times, e.g. more than three or four times, the machine issues a warning that recirculation may have occurred or a measurement of this recirculation can be automatically initiated by the machine. A meaningful assumption for the threshold value can be determined from a desired treatment time and a desired Kt/V value, or from a (desired) treatment time and a Kt/V value of previous treatments, or from a (desired) treatment time and a Kt/V value theoretically calculated by Watson-V, wherein the dialyzer must be known.

A similar procedure is also possible with raw signals, i.e. an intensity or absorbance (absorption value). Similarly, the search for specific patterns could also be used using known distance measures to detect specific features or indicators within the respective curves. In addition, the combination of features could contribute to an increase in the robustness of the triggering, as well as the matching with certain other state variables of the machine, because certain features are generated also by parameter changes on the machine sometimes. A matching of the machine state for the point in time at which a feature is detected can also serve as a plausibility check here.

Examples for further features are described below: If there is a volatile/jumping Kt/V progression curve as well as, for example, a venous pressure that also exceeds a defined, possibly patient-specific limit value (e.g. 150 mmHg), this would be an additional indication of a change in the vessel access. Strongly increased venous pressures can be an indicator for discharge stenoses. If there are no strong variations in the Kt/V curve, but its increase is significantly steeper than the expected increase for the respective patient, this can also serve as a trigger event (i.e. as a release scheme for the output of a trigger or trigger signal). This means that the Kt/V curve can be significantly above a predicted linear treatment course (Kt/V signal course), so that the Kt/V target of 1.2, for example, appears to be reached after 60% of the treatment time. In such a case, the exceeding of an absolute threshold value for the increase of the Kt/V curve/the Kt/V signal course could serve as a trigger variable (indicator). Alternatively, a determination of the intersection of the desired Kt/V curve with the actual Kt/V curve or the predicted Kt/V curve (extrapolated from the currently available Kt/V data) could serve as a criterion. If this intersection point on the time axis is significantly ahead of the estimated time, this can serve as an indication that a significant recirculation is present. Since patient movements can lead to fluctuations in pressures, but also to fluctuations in the Kt/V curve, an additional analysis of simultaneously occurring large fluctuations of the arterial and venous pressure provides an indication for such a movement. If a high venous pressure, a peak/signal peak in the derivative of the Kt/V curve/the differential signal or similar is subsequently observed, recirculation measurement can be initiated.

BRIEF DESCRIPTION OF THE DRAWING FIGURES

In the following, an embodiment of the present invention is described in more detail on the basis of the attached Figures. These are merely illustrative and are not intended to limit the scope of the present invention.

DETAILED DESCRIPTION

FIGS. 1a to 1f each show a diagram in which a course of a Kt/V signal $Kt/V_{Actual}$ over time t is represented as a solid line. Furthermore, a desired Kt/V value $Kt/V_{Desired}$ of 1.2 is marked in the diagram. A dashed line indicates a theoretical linear Kt/V course $Kt/V_{theo}$, with which the desired Kt/V value $Kt/V_{Desired}$ is reached at a defined desired treatment time $t_{Desired}$. These Figures differ as described in the following with regard to the signal characteristics illustrated.

Figure 1:
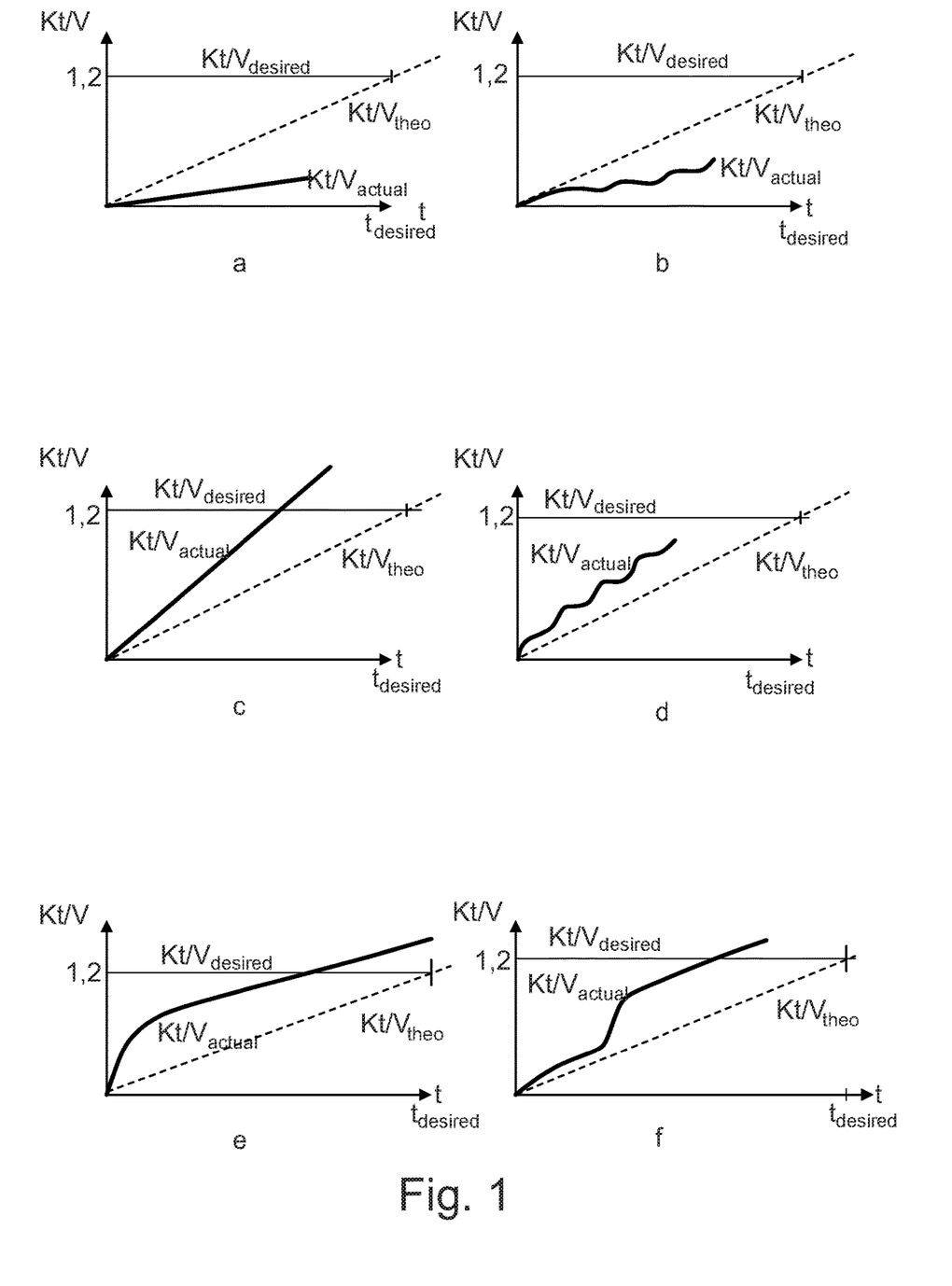
FIGS. 1a-1f show Kt/V signal courses according to an embodiment of the invention, which may indicate a present recirculation.

FIG. 1a shows a flat signal course of the Kt/V signal $Kt/V_{Actual}$. The Kt/V signal $Kt/V_{Actual}$ is much flatter than the theoretical Kt/V course $Kt/V_{theo}$ and the desired Kt/V value $Kt/V_{Desired}$ is not expected to be reached within the desired treatment time $t_{Desired}$. This can be an indication of a present recirculation, since in this case the blood flowing through the filter, which must actually be cleaned, is diluted by the already cleaned, recirculated blood. In this way, a concentration of pollutants dissolved in the blood decreases much more slowly than expected, which can be measured in the used dialysis liquid e.g. by means of the ADIMEA™ brand system from B. Braun. Accordingly, the Kt/V signal $Kt/V_{Actual}$ shown in FIG. 1a serves as an indicator for an existing recirculation. FIG. 1b shows a flat signal course, similar to FIG. 1a, which in addition is volatile or unsteady. A signal course without jumps as in FIG. 1a occurs more frequently in a treatment with a catheter connected to the patient than in extracorporeal blood treatments. The unsteady course shown in FIG. 1b may indicate turbulences in a shunt through which a patient is connected to the extracorporeal blood treatment machine, or may indicate frequent movements of the patient. Also this circumstance, both in combination with the flat signal course and as a stand-alone feature, may indicate an existing recirculation and as an indicator for it. In other words, a constant recirculation will be indicated by a jumping curve and a poor treatment outcome. This can be identified by observing repetitive, short-term changes in the slope of the curve and the poor treatment outcome (for a longer-term trend or prognosis of the signal or Kt/V value at the end of the treatment).

FIG. 1c shows a strongly increasing signal course of the Kt/V signal $Kt/V_{Actual}$. The Kt/V signal $Kt/V_{Actual}$ is significantly steeper than the theoretical Kt/V course $Kt/V_{theo}$, and the desired Kt/V value $Kt/V_{Desired}$ is expected to be reached well before the desired treatment time $t_{Desired}$ is reached. This can be an indication of an existing, increasing recirculation, since in this case an increasing amount of already purified blood flows back through the shunt into the extracorporeal blood treatment machine, so that the blood flowing through the filter, which still has to be cleaned, is increasingly diluted by already purified, recirculated blood. In this way, a Kt/V measuring cell measuring the Kt/V signal $Kt/V_{Actual}$ determines a steady decrease of the concentration of pollutants, which basically indicates a successful extracorporeal blood treatment, although the decrease of the concentration of pollutants is mainly due to the increasing recirculation and the actual treatment result deteriorates increasingly. This is mostly noticeable by the fact that the extracorporeal blood treatment appears to be much more efficient than expected. Accordingly, a Kt/V signal course that increases far too much can also be an indicator for an existing recirculation. FIG. 1d shows a steep signal course according to FIG. 1c, which additionally, as already described in more detail in the context of FIG. 1b, is volatile or unsteady, which can serve as an indicator for an existing recirculation either alone or in combination with a steep signal course. In other words, an increasing recirculation is indicated by a jumping signal and a good treatment result, which reflects the increasing degree of recirculation. Indicators are thus short-term changes in the slope of the signal course and the treatment result which is too good (for a longer-term trend or a prognosis of the signal or Kt/V value at the end of the treatment).

FIG. 1e and FIG. 1f each show a Kt/V signal $Kt/V_{Actual}$ in the course of which a sudden, strong increase occurs. In FIG. 1e, this increase occurs at the beginning of the measurement, whereas in FIG. 1f it only occurs in the course of the measurement. Such a sudden, strong increase of the Kt/V signal $Kt/V_{Actual}$ can be attributed to the fact that in the case of recirculation the blood to be purified is suddenly diluted by the recirculated, already purified blood. Accordingly, the concentration of pollutants in the blood decreases, resulting in a sudden increase in the Kt/V value which is determined by measuring the used dialysis liquid. Thus, such a sudden, strong increase of the Kt/V signal can also serve as an indicator for an existing recirculation.

Figure 2:
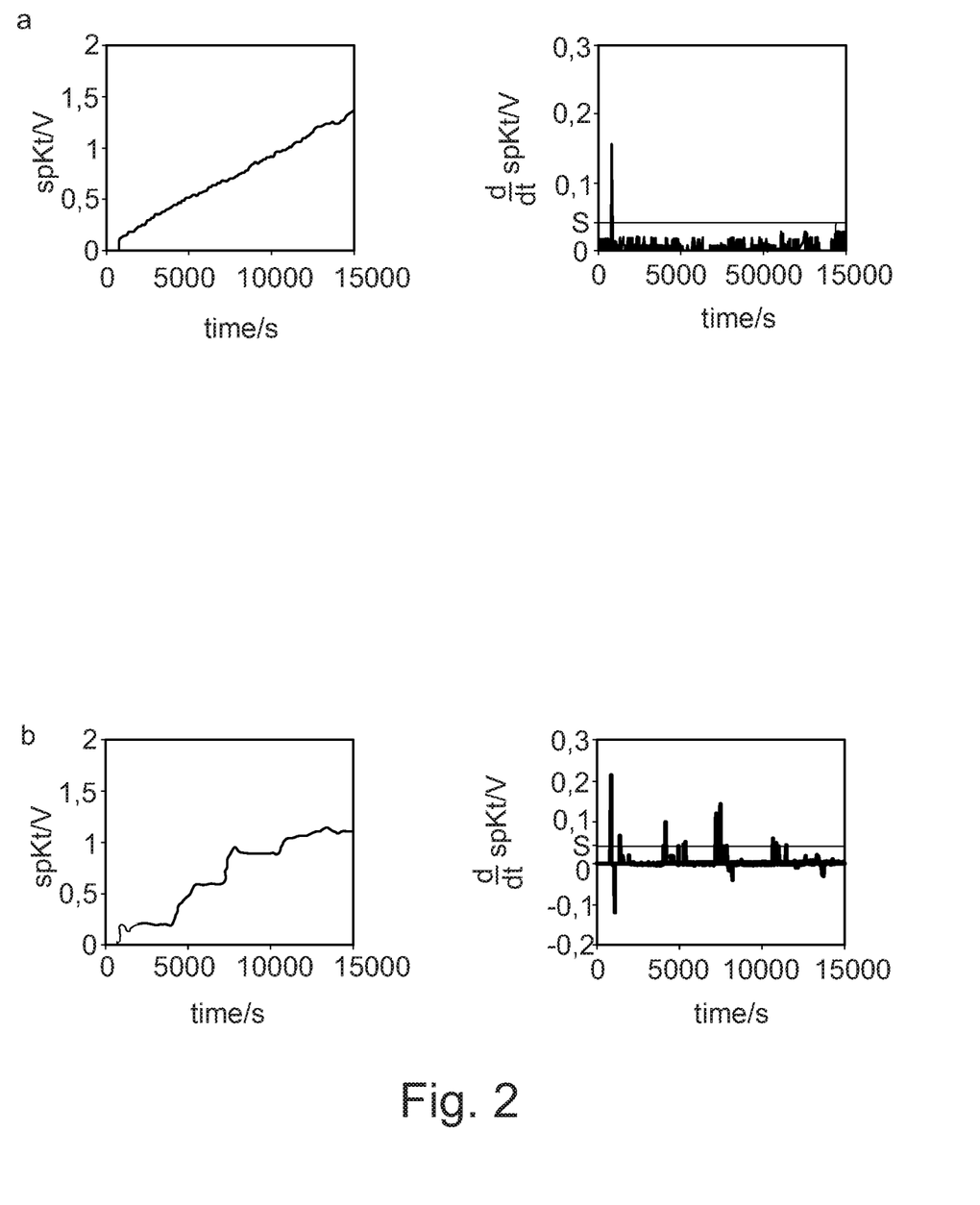
FIG. 2a shows a typical, recirculation-free spKt/V signal course and its derivation.
FIG. 2b shows a jumping spKt/V signal course and its derivation.

FIG. 2a shows a typical, recirculation-free Kt/V signal (left), in particular a spKt/V signal, as it is recorded, for example, by the ADIMEA™ brand system from B. Braun, and its derivative (right), wherein the derivative was calculated in regular, relatively short time intervals. It can be seen that the recirculation-free Kt/V signal increases essentially linearly. It is only at the beginning of the measurement and towards the end of the spKt/V signal course shown here that irregularities occur, wherein the former can be attributed to a slightly delayed start of the measurement. These irregularities are represented as signal peaks in the derivative of the spKt/V signal, which otherwise runs essentially uniformly with a mean slope starting from zero. A threshold value S is defined such that the derivative of a theoretical or linear spKt/V signal course is always lower. The two signal peaks of the derivative of the spKt/V signal (of the differential signal) occurring in FIG. 2a reach or exceed this threshold value S.

FIG. 2b shows the corresponding Kt/V signal (left), in particular the spKt/V signal, in a case where recirculation may have occurred, and the derivative (right) of the signal, wherein the derivative was calculated at regular, relatively short time intervals. It can be seen that the Kt/V signal jumps strongly in this case. These jumps or irregularities result in a strongly fluctuating derivative of the spKt/V signal with a multitude of both positive and negative signal peaks. The threshold value S, which is defined such that the derivative of a normal, recirculation-free spKt/V signal course is always lower, is often reached and exceeded. If there is a certain number, e.g. three or four, of such exceedances of the threshold value S, this is seen as an indicator for an existing recirculation.

Figure 3:
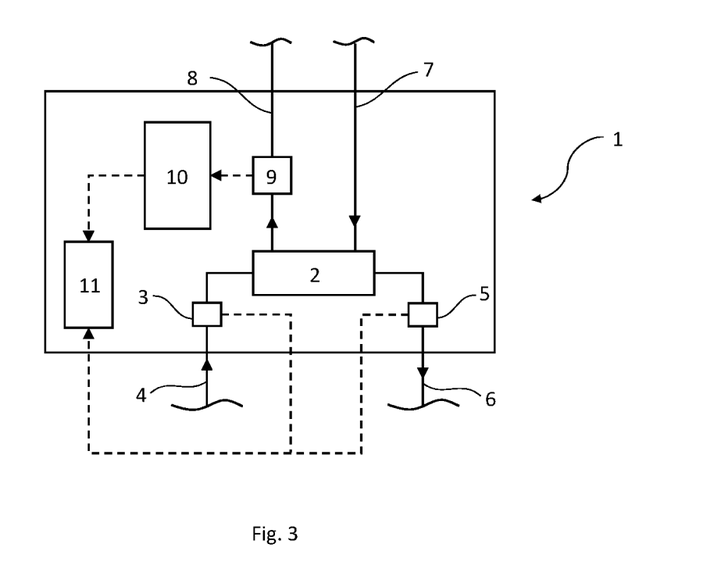
FIG. 3 schematically shows an extracorporeal blood treatment machine with a monitoring device according to the invention.
Figure 4:
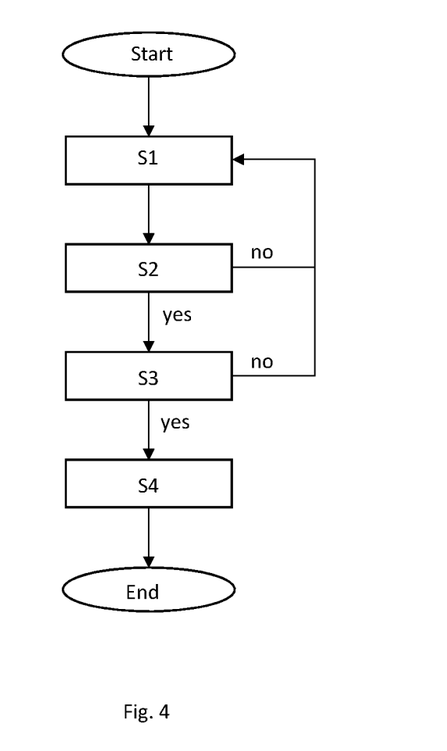
FIG. 4 shows a flow chart illustrating a procedure for determining and processing a recirculation indicator.

FIG. 3 schematically shows an extracorporeal blood treatment machine 1. During an extracorporeal blood treatment, blood from a patient is supplied to a filter 2 or dialyzer via a blood supply line 4 having an arterial pressure sensor 3, and the blood from the filter 2 is returned to the patient via a blood discharge line 6 having a venous pressure sensor 5. The blood flows through the filter 2, with pollutants from the blood passing through a semipermeable membrane into a dialysis liquid flowing through the filter 2 in the counter-current principle. For this purpose, fresh dialysis liquid is fed through a dialysis liquid supply line 7 into the filter 2 and the used dialysis liquid is discharged from the filter 2 through a dialysis liquid discharge line 8. In the dialysis liquid discharge line 8, a Kt/V measuring cell 9 is arranged, which measures the Kt/V signal course during an extracorporeal blood treatment preferably continuously. This Kt/V measuring cell 9 transmits the Kt/V signal to a monitoring device 10 (alternatively, the Kt/V measuring cell 9 can be part of the monitoring device 10), which then performs the method described below with reference to FIG. 4.

The monitoring device 10 receives or determines the Kt/V signal in step S1. In step S2, the signal is analyzed as described for example with reference to FIGS. 2a and 2b and it is determined whether one of the indicators for an existing recirculation described above with reference to FIG. 1a to 1f is present. If no such indicator is determined (marked "no" in FIG. 4), the monitoring device 10 returns to step S1. However, if one of the indicators is determined (marked "yes" in FIG. 4), a plausibility check is carried out with step S3, wherein further sensor data, e.g. measured values of the venous pressure sensor 5 and if applicable of the arterial pressure sensor 7, current operating parameters of the extracorporeal blood treatment machine 1, or the presence of further indicators are checked to determine whether the presence of recirculation can be a plausible cause for the occurrence of the indicator determined in step S2. If the plausibility check is negative (marked "no" in FIG. 4), the monitoring device 10 returns to step S1. However, if the plausibility check is positive (marked "yes" in FIG. 4), step S4 outputs a trigger or trigger signal, which is either directly output to a recirculation measuring cell 11, whereby an accurate, reliable recirculation measurement is initiated automatically, by means of which a request to initiate a recirculation measurement is automatically output to a user, e.g. via a display or an audible signal.

The invention claimed is:

1. An extracorporeal blood treatment machine comprising:
    a filter having a blood inlet line configured to receive blood from a patient, a blood outlet line configured to return the blood to the patient, a dialysis liquid inlet line configured to receive fresh dialysis liquid, a dialysis liquid outlet line configured to discharge used dialysis liquid, and a semipermeable membrane configured to filter pollutants from the blood into the fresh dialysis liquid to convert the fresh dialysis liquid into the used dialysis liquid;
    a measuring cell in the dialysis liquid outlet line; and
    a monitoring device operatively connected to the measuring cell, wherein the monitoring device is configured to:
        detect a signal from the measuring cell continuously representing a concentration of pollutants in the used dialysis liquid and to automatically evaluate a signal course with respect to at least one predetermined signal course indicator or signal course pattern for an existing blood recirculation;
        differentiate the signal for evaluation in order to calculate a differential signal and compare it with a threshold value, wherein a certain frequency or duration of threshold value overruns and/or a one-time threshold value overrun of said threshold value or of another threshold value is recognized as the at least one predetermined signal course indicator or signal course pattern for the existing blood recirculation; and automatically initiate a recirculation measurement or automatically output a request for initiating a recirculation measurement to a user upon determination of the at least one predetermined signal course indicator or signal course pattern.

2. The extracorporeal blood treatment machine according to claim 1, wherein the signal represents a Kt/V value or is a raw signal from which the Kt/V value is calculated.

3. The extracorporeal blood treatment machine according to claim 1, wherein the threshold value depends on a desired treatment time and a desired signal value and/or a signal value of a previous extracorporeal blood treatment and/or a theoretically calculated signal value.

4. The extracorporeal blood treatment machine according to claim 1, wherein the monitoring device is further configured for calculating, from the signal, an expected treatment time at which a desired signal value is expected to be reached, and for comparing the expected treatment time with a desired treatment time, wherein a clear shortfall or a clear overshoot of the desired treatment time serves as the at least one predetermined signal course indicator or signal course pattern for the existing blood recirculation.

5. The extracorporeal blood treatment machine according to claim 1, wherein the monitoring device is further configured for comparing the signal course with previously stored reference patterns or patterns of the signal course which occur with an existing blood recirculation, and to recognize a sufficient correspondence of the signal with the previously stored reference patterns or patterns of the signal course as the at least one predetermined signal course indicator or signal course pattern for the existing blood recirculation.

6. The extracorporeal blood treatment machine according to claim 1, wherein the monitoring device is further configured to initiate a plausibility check after determining the at least one predetermined signal course indicator or signal course pattern.

7. The extracorporeal blood treatment machine according to claim 6, wherein the monitoring device is, within a framework of the plausibility check, further configured for comparing an occurrence of the at least one predetermined signal course indicator or signal course pattern with further sensor data, a change in an operational state or parameter of the extracorporeal blood treatment machine, or a theoretically calculated signal course.

8. The extracorporeal blood treatment machine according to claim 6, wherein the at least one predetermined signal course indicator or signal course pattern comprises a plurality of signal course indicators or signal course patterns that are determined and compared within a framework of the plausibility check.

9. A monitoring method for operating an extracorporeal blood treatment machine comprising: a filter having a blood inlet line configured to receive blood from a patient, a blood outlet line configured to return the blood to the patient, a dialysis liquid inlet line configured to receive fresh dialysis liquid, a dialysis liquid outlet line configured to discharge used dialysis liquid, and a semipermeable membrane configured to filter pollutants from the blood into the fresh dialysis liquid to convert the fresh dialysis liquid into the used dialysis liquid; a measuring cell in the dialysis liquid outlet line; and a monitoring device operatively connected to a measuring cell, the monitoring method comprising the steps of:
  detecting a signal course from the measuring cell representing a concentration of pollutants in a used dialysis liquid;
  automatically evaluating, by the monitoring device, the signal course with respect to at least one predetermined signal course indicator or signal course pattern for an existing blood recirculation; and
  automatically initiating, by the monitoring device, a recirculation measurement or outputting an automatic request for initiating a recirculation measurement to a user if the at least one predetermined signal course indicator or signal course pattern has been determined.

10. The monitoring method according to claim 9, further comprising initiating a plausibility check by the monitoring device.

11. The monitoring method according to claim 10, wherein initiating the plausibility check is performed immediately after the at least one predetermined signal course indicator or signal course pattern has been determined.

* * * * *